(12) United States Patent  (10) Patent No.: US 9,371,462 B2
Watanabe et al.  (45) Date of Patent: Jun. 21, 2016

(54) PRODUCTION PROCESS FOR SELF-DISPERSIBLE PIGMENT, SELF-DISPERSIBLE PIGMENT, INK, INK CARTRIDGE AND INK JET RECORDING METHOD

(71) Applicant: CANON KABUSHIKI KAISHA, Tokyo (JP)

(72) Inventors: Taiki Watanabe, Akishima (JP); Koichi Suzuki, Yokohama (JP); Ryuji Higashi, Kawasaki (JP); Masashi Hirose, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/747,343

(22) Filed: Jun. 23, 2015

(65) Prior Publication Data

US 2015/0376426 A1  Dec. 31, 2015

(30) Foreign Application Priority Data

Jun. 30, 2014 (JP) ................. 2014-133777

(51) Int. Cl.
 *C09D 11/322* (2014.01)
 *C07C 241/02* (2006.01)
 (Continued)

(52) U.S. Cl.
 CPC ........... *C09D 11/322* (2013.01); *B41J 2/01* (2013.01); *C07C 241/02* (2013.01); *C07D 471/04* (2013.01); *C07F 9/3834* (2013.01); *C07F 9/3873* (2013.01); *C09D 11/324* (2013.01)

(58) Field of Classification Search
 CPC .............. B41J 2/01; B41J 2/0057; B41J 2/05; B41J 2/1433; B41J 2/17; B41J 2/1755; B41J 2/17503; B41J 2/17593; B41J 2/21; B41J 2/211; B41J 2/2107; B41J 2/2114; B41J 2/2117; B41J 2/2056; B41J 11/0015; B41J 11/002; B41J 3/60; B41M 5/0011; B41M 5/0017; B41M 5/0256; B41M 5/52; B41M 5/5218; B41M 7/00; B41M 7/0072; B41M 7/0081; B41M 7/009; C09D 11/005; C09D 11/30; C09D 11/32; C09D 11/322; C09D 11/328; C09D 11/36; C09D 11/38; C09D 11/40; C09D 11/52; C09D 11/54; C09D 11/101; C07C 241/02; C07D 471/04; C07F 9/3834
 USPC ........................ 347/9–22, 56, 86, 88, 95–105; 106/31.13, 31.27, 31.6, 31.85, 31.77; 523/160, 161
 See application file for complete search history.

(56) References Cited

U.S. PATENT DOCUMENTS 5,570,120 A  10/1996 Sakaki et al.
5,591,514 A  1/1997 Hirose et al.
(Continued)

FOREIGN PATENT DOCUMENTS

JP  H10-510861 A  10/1998
JP  2012-528917 A  11/2012

OTHER PUBLICATIONS

Epson C-88 User manual, Epson America Inc, May 2005, pp. 23-28.*
(Continued)

*Primary Examiner* — Matthew Luu
*Assistant Examiner* — Rut Patel
(74) *Attorney, Agent, or Firm* — Fitzpatrick, Cella, Harper & Scinto

(57) ABSTRACT

The invention provides a production process for a self-dispersible pigment, having a step of bonding a group $R_1$ in the following general formula (1) to a particle surface of a pigment by radical addition reaction induced by removal of a hydrogen atom from a compound represented by the general formula (1):

$$HN=N-R_1 \quad (1)$$

wherein $R_1$ is a group having at least one of an aliphatic group and an aromatic group and being substituted with at least one hydrophilic group selected from the group consisting of a carboxylic acid group, a sulfonic acid group, a phosphoric acid group and a phosphoric acid group.

15 Claims, 3 Drawing Sheets

(51) Int. Cl.
*C07D 471/04* (2006.01)
*B41J 2/01* (2006.01)
*C09D 11/324* (2014.01)
*C07F 9/38* (2006.01)

(56) References Cited

U.S. PATENT DOCUMENTS

| | | | |
|---|---|---|---|
| 5,601,928 A | 2/1997 | Katayama et al. | |
| 5,851,280 A | 12/1998 | Belmont et al. | |
| 5,900,029 A | 5/1999 | Belmont et al. | |
| 5,908,728 A | 6/1999 | Sakaki et al. | |
| 5,939,210 A | 8/1999 | Hirose et al. | |
| 5,954,906 A | 9/1999 | Abe et al. | |
| 6,042,643 A | 3/2000 | Belmont et al. | |
| 6,084,006 A | 7/2000 | Kashiwazaki et al. | |
| 6,162,510 A | 12/2000 | Kashiwazaki et al. | |
| 6,174,056 B1 | 1/2001 | Sakaki et al. | |
| 6,203,604 B1 | 3/2001 | Kashiwazaki et al. | |
| 6,203,899 B1 | 3/2001 | Hirose et al. | |
| 6,248,482 B1 | 6/2001 | Kashiwazaki et al. | |
| 6,475,601 B1 | 11/2002 | Sakaki et al. | |
| 6,494,946 B1 | 12/2002 | Belmont et al. | |
| 6,500,523 B1 | 12/2002 | Hirose et al. | |
| 6,521,034 B1 | 2/2003 | Osumi et al. | |
| 6,521,323 B1 | 2/2003 | Sakaki et al. | |
| 6,528,146 B2 | 3/2003 | Okuda et al. | |
| 6,533,852 B2 | 3/2003 | Hirose | |
| 6,547,381 B2 | 4/2003 | Watanabe et al. | |
| 6,585,366 B2 | 7/2003 | Nagata et al. | |
| 6,706,105 B2 | 3/2004 | Watanabe et al. | |
| 6,740,151 B2 | 5/2004 | Belmont et al. | |
| 6,802,925 B2 | 10/2004 | Kobayashi et al. | |
| 6,921,433 B2 | 7/2005 | Kuribayashi et al. | |
| 7,005,461 B2 | 2/2006 | Sanada et al. | |
| 7,160,376 B2 | 1/2007 | Watanabe et al. | |
| 7,294,185 B2 | 11/2007 | Belmont et al. | |
| 7,371,274 B2 | 5/2008 | Sanada et al. | |
| 7,423,075 B2 | 9/2008 | Ikegami et al. | |
| 7,442,753 B2 | 10/2008 | Tsubaki et al. | |
| 7,449,513 B2 | 11/2008 | Sato et al. | |
| 7,498,364 B2 | 3/2009 | Sato et al. | |
| 7,504,488 B2 | 3/2009 | Toyoda et al. | |
| 7,528,179 B2 | 5/2009 | Suda et al. | |
| 7,528,182 B2 | 5/2009 | Teshima et al. | |
| 7,538,147 B2 | 5/2009 | Sato et al. | |
| 7,563,853 B2 | 7/2009 | Tsubaki et al. | |
| 7,598,332 B2 | 10/2009 | Ikegami et al. | |
| 7,601,790 B2 | 10/2009 | Sato et al. | |
| 7,605,192 B2 | 10/2009 | Sanada et al. | |
| 7,704,414 B2 | 4/2010 | Sato et al. | |
| 7,754,000 B2 | 7/2010 | Nakahama et al. | |
| 7,866,806 B2 | 1/2011 | Sato et al. | |
| 7,914,616 B2 | 3/2011 | Nakahama et al. | |
| 8,007,097 B2 | 8/2011 | Sanada et al. | |
| 8,177,902 B2 | 5/2012 | Nakahama et al. | |
| 8,343,269 B2 | 1/2013 | Takahashi et al. | |
| 8,450,393 B2 | 5/2013 | Tsubaki et al. | |
| 8,580,024 B2 | 11/2013 | Gu | |
| 8,672,465 B2 | 3/2014 | Sanada et al. | |
| 8,899,736 B2 | 12/2014 | Sanada et al. | |
| 2003/0095914 A1 | 5/2003 | Belmont et al. | |
| 2003/0195291 A1* | 10/2003 | Lamprey | C09C 1/56 524/495 |
| 2005/0034629 A1 | 2/2005 | Belmont et al. | |
| 2005/0131102 A1 | 6/2005 | Nakazawa et al. | |
| 2005/0197424 A1 | 9/2005 | Higashi et al. | |
| 2005/0239918 A1 | 10/2005 | Nakazawa et al. | |
| 2006/0050117 A1 | 3/2006 | Sato et al. | |
| 2006/0100310 A1 | 5/2006 | Nakazawa et al. | |
| 2006/0160975 A1 | 7/2006 | Suda et al. | |
| 2006/0250463 A1 | 11/2006 | Nakazawa et al. | |
| 2009/0182076 A1 | 7/2009 | Teshima et al. | |
| 2010/0307377 A1* | 12/2010 | Gu | C09D 11/322 106/31.75 |
| 2015/0029241 A1 | 1/2015 | Sanada et al. | |

OTHER PUBLICATIONS

Gever, Gabriel, "Hydrazinoalkanols," Journal of The American Chemical Society, vol. 76, Mar. 5, 1954, pp. 1283-1285.

Taniguchi, Tsuyoshi, "Iron-Catalyzed Oxidative Addition of Alkoxycarbonyl Radicals to Alkenes with Carbazates and Air," Angewandte Chemie International Edition, Edition 49, 2010, pp. 10154-10157.

* cited by examiner

PRODUCTION PROCESS FOR SELF-DISPERSIBLE PIGMENT, SELF-DISPERSIBLE PIGMENT, INK, INK CARTRIDGE AND INK JET RECORDING METHOD

BACKGROUND OF THE INVENTION

1. Field of the Invention

The present invention relates to a production process for a self-dispersible pigment, a self-dispersible pigment, an ink, an ink cartridge and an ink jet recording method.

2. Description of the Related Art

A self-dispersible pigment is mainly produced by a chemical pigment-modifying technology. For example, Japanese Patent Application Laid-Open No. H10-510861 describes a process for obtaining a self-dispersible pigment by causing a pigment to react with a diazonium salt. In addition, Japanese Patent Application Laid-Open No. 2012-528917 describes a process for obtaining a self-dispersible pigment by subjecting a carbonyl group on a particle surface of a pigment and a hydrazine compound to a condensation reaction.

However, the conventional pigment-modifying technologies have not satisfied a production process with high safety and reaction efficiency taking environmental burdens which have been regarded as important in recent years into consideration. In, for example, the production process described in Japanese Patent Application Laid-Open No. H10-510861, a nitrite low in stability and the like is utilized. In addition, residue of the nitrite and a nitrogen oxide may occur in some cases in the process of treating a pigment with a diazonium salt. Further, reaction efficiency is hard to be improved due to bubbles generated during reaction. In addition, the production process described in Japanese Patent Application Laid-Open No. 2012-528917 has involved a problem that reaction efficiency is low due to influence of the number of groups present on the particle surface of the pigment and reactivity thereof.

SUMMARY OF THE INVENTION

Accordingly, it is an object of the present invention to provide a production process with high reaction efficiency for a self-dispersible pigment useful as a coloring material for an ink or the like. In addition, another object of the present invention is to provide a self-dispersible pigment produced by the above-described production process for the self-dispersible pigment, an ink using this self-dispersible pigment, and an ink cartridge and an ink jet recording method using this ink.

The above objects can be achieved by the present invention described below. According to the present invention, there is thus provided a production process for a self-dispersible pigment, comprising a step of bonding a group $R_1$ in the following general formula (1) to a particle surface of a pigment by radical addition reaction induced by removal of a hydrogen atom from a compound represented by the following general formula (1):

$$HN=N-R_1 \quad (1)$$

wherein $R_1$ is a group having at least one of an aliphatic group and an aromatic group and being substituted with at least one hydrophilic group selected from the group consisting of a carboxylic acid group, a sulfonic acid group, a phosphoric acid group and a phosphoric acid group.

According to the present invention, there can be provided a production process with high reaction efficiency for a self-dispersible pigment useful as a coloring material for an ink or the like. In addition, according to another embodiment of the present invention, there can be provided a self-dispersible pigment produced by this production process for the self-dispersible pigment, an ink using this self-dispersible pigment, and an ink cartridge and an ink jet recording method using this ink.

Further features of the present invention will become apparent from the following description of exemplary embodiments with reference to the attached drawings.

BRIEF DESCRIPTION OF THE DRAWINGS

FIGS. 5A and 5B schematically illustrate an example of an ink jet recording apparatus used in an ink jet recording method according to the present invention, in which

DESCRIPTION OF THE EMBODIMENTS

Preferred embodiments of the present invention will now be described in detail in accordance with the accompanying drawings. However, the present invention is not limited to the following embodiments. Incidentally, when an ionic group forms a salt, the ionic group may be present in a state of being dissociated into an ion in an ink. However, such a group is represented as "ionic group" for convenience's sake in the present invention. In addition, a self-dispersible pigment may be described as "pigment" merely. Various physical property values in the present specification are values at ordinary temperature (25° C.) unless expressly noted.

Production Process for Self-Dispersible Pigment:

The production process for a self-dispersible pigment according to the present invention has a step of bonding a group $R_1$ in the following general formula (1) to a particle surface of a pigment by radical addition reaction induced by removal of a hydrogen atom from a compound represented by the general formula (1):

$$HN=N-R_1 \quad (1)$$

wherein $R_1$ is a group having at least one of an aliphatic group and an aromatic group and being substituted with at least one hydrophilic group selected from the group consisting of a carboxylic acid group, a sulfonic acid group, a phosphoric acid group and a phosphoric acid group.

According to the production process for a self-dispersible pigment according to the present invention (hereinafter also referred to as "production process" merely), the self-dispersible pigment can be produced by one-pot synthesis with high reaction efficiency even at ordinary temperature (25° C.) without using a specific reaction apparatus or a specific liquid medium. Since the reaction efficiency is high in particular, a self-dispersible pigment with a high introduced amount of a functional group can be obtained while reducing the use amount of a treatment agent for the pigment. In addition, since the generation of a byproduct is inhibited, purification after the production is also easy. Moreover, the use of the stable treatment agent can reduce burdens on the environment, unlike the conventional production process for a self-dispersible pigment.

The reaction efficiency in the present invention can be calculated according to, for example, the following procedure. Upon the production of the self-dispersible pigment, "molar number of hydrophilic group in treatment agent" is calculated from the molar number of the treatment agent used per 1.0 g of the pigment. This "molar number of hydrophilic group in treatment agent" is the molar number of the hydrophilic group of the treatment agent used per 1.0 g of the pigment. For example, when a compound having two carboxylic acid groups in its molecule is used as the treatment agent, the calculation is made with the molar number regarded as being twice of the molar number determined by utilizing the molecular weight of this treatment agent. In addition, with respect to the self-dispersible pigment produced, the amount of the hydrophilic group contained in a functional group on a particle surface of the pigment ("molar number of hydrophilic group in pigment", value per 1.0 g of the pigment) is determined. When a treatment agent having a hydrophilic group in the form of an anhydride is used, such a hydrophilic group in the self-dispersible pigment produced becomes an anionic group, so that "molar number of hydrophilic group" in the treatment agent and the pigment is calculated as a molar number of the anionic group. The reaction efficiency can be calculated from "molar number of hydrophilic group in pigment" and "molar number of hydrophilic group in treatment agent" obtained above according to the following expression (A).

Reaction efficiency (%)=("Molar number of hydrophilic group in pigment"/"Molar number of hydrophilic group in treatment agent")×100      (A)

Higher reaction efficiency means that a pigment can be modified into a self-dispersible pigment with a less used amount of the treatment agent. Therefore, the high reaction efficiency enables not only having an advantage from the viewpoint of cost, but also reducing the generation of impurities caused by the reaction. Moreover, purification efficiency of an aqueous dispersion liquid containing the self-dispersible pigment can also be improved. In addition, when an ink containing the self-dispersible pigment produced as a coloring material is applied to, for example, an ink jet recording method, lowering of ejection characteristics caused by impurities can be inhibited. Therefore, the reaction efficiency is favorably made as high as possible. Specifically, the reaction efficiency is favorably 10% or more, more favorably 20% or more, particularly favorably 30% of more. Incidentally, the theoretical upper limit of the reaction efficiency is 100%.

The production process according to the present invention is a process for producing a self-dispersible pigment by bonding a group $R_1$ which is a functional group containing a hydrophilic group to a particle surface of a pigment by radical addition reaction induced by removal of a hydrogen atom from a compound represented by the general formula (1) (diazene compound). This radical addition reaction is an oxidative radical addition reaction. In addition, it is favorable in the present invention that the compound represented by the general formula (1) is formed by removal of a hydrogen atom from a compound represented by the following general formula (2) (hydrazine compound). That is, a self-dispersible pigment can also be produced by a radical addition reaction through sequential removal of hydrogen atoms from the compound represented by the general formula (2).

$$H_2N-NH-R_1 \quad (2)$$

wherein $R_1$ is a group having at least one of an aliphatic group and an aromatic group and being substituted with at least one hydrophilic group selected from the group consisting of a carboxylic acid group, a sulfonic acid group, a phosphoric acid group and a phosphoric acid group.

An estimated mechanism of a reaction used in the production process according to the present invention is shown below. The description will hereinafter be made taking a case where a compound represented by the general formula (2) is used as the treatment agent and carbon black is used as the pigment, and potassium hexacyanoferrate(III) is used as an oxidizing agent, as an example. Incidentally, the oxidized species and reduced species of potassium hexacyanoferrate (III) used as the oxidizing agent are expressed as $Fe^{3+}$ and $Fe^{2+}$, respectively.

The reaction mechanism has been estimated by referring to Angewandte Chemie International Edition, 49, 10154-10157 (2010). This reference describes a reaction mechanism of an oxidative radical addition reaction with respect to olefins.

self-dispersible pigment

First, a hydrogen atom is removed from a compound A which is a hydrazine compound (compound represented by the general formula (2)) by the action of the oxidizing agent ($Fe^{3+}$), and thus the compound A is radically oxidized to form a hydrazyl radical B. A hydrogen atom is then removed from the hydrazyl radical B by the action of the oxidizing agent ($Fe^{3+}$) to form a compound C which is a diazene compound (compound represented by the general formula (1)). A hydrogen atom is further removed from the compound C by the action of the oxidizing agent ($Fe^{3+}$) to form a diazene radical D. The diazene radical D instantly gives rise to denitrification to form a radical species E. The radical species E then causes radical addition to an aromatic carbon atom on a particle surface of carbon black, whereby $R_1$ is bonded to the particle surface of carbon black through a radical intermediate F to obtain a self-dispersible pigment G.

When an oxidizing agent whose valence is liable to vary, such as potassium hexacyanoferrate(III), is used in the production process according to the present invention, another addition reaction than the above may occur in parallel in some cases. That is, at the same time when the radical species E causes radical addition to the aromatic carbon atom on the particle surface of carbon black to form the radical intermediate F, the radical is captured by an oxygen molecule, thereby forming a radical intermediate H. In this case, after the radical intermediate H is reduced by the action of a reducing species ($Fe^{2+}$) of the oxidizing agent, a self-dispersible pigment J which is in the form of an alcohol is obtained through an oxygen radical intermediate I.

In the above-described reaction mechanism, the diazene compound or the hydrazine compound is not rapidly decomposed, but the radical species is slowly formed, so that the radical addition reaction with respect to the particle surface of the pigment is caused to efficiently progress. According to the production process of the present invention, a self-dispersible pigment with a high introduced amount of a functional group can be thus obtained even when the use amount of the treatment agent for the pigment is small compared with the conventional production processes for the self-dispersible pigment. Therefore, the resultant self-dispersible pigment has high dispersion stability.

In Japanese Patent Application Laid-Open No. H10-510861, a self-dispersible pigment is produced by using a diazonium salt as the treatment agent. However, the diazonium salt used as the treatment agent is easily decomposed by influence of an alkali or a temperature exceeding ordinary temperature (25° C.). When the diazonium salt is decomposed in the reaction system, various decomposed products are produced. Therefore, various side reactions such as a reaction of the decomposed product with a liquid medium or oxygen, a reaction between the decomposed products, and other side reactions than these reactions are easy to occur. Accordingly, when it is attempted to obtain the self-dispersible pigment with the high introduced amount of the functional group by using the diazonium salt, it is necessary to use the diazonium salt in an amount more than that of the pigment. However, when the amount of the diazonium salt used is increased, many nitrogen gas bubbles are generated, so that it is hard to improve the reaction efficiency.

Since the compound represented by the general formula (2) is chemically stable and hardly influenced by pH or temperature, the pH or temperature of the reaction system may be arbitrarily set. Specifically, the pH of the reaction system is favorably 1 or more and 13 or less, more favorably 1 or more and 10 or less. Above all, the pH of the reaction system is more favorably 1.5 or more and 7 or less, particularly favorably 2 or more and 7 or less. The pH of the reaction system is favorably set to be from acidic to neutral for improving the reaction efficiency. In a high pH range such as alkalinity, the treatment agent may be decomposed in some cases. On the other hand, when the pH of the reaction system is set to less than 1.5 or less than 2.0, the solubility of the treatment agent tends to be lowered, so that the reaction efficiency may be lowered in some cases, or it is necessary to use an acidic compound in plenty. Thus, treatment such as purification of the resulting self-dispersible pigment may become difficult in some cases.

In order to control the reaction rate of the radical addition reaction, the temperature may also be set to another temperature than ordinary temperature (25° C.) The temperature may be suitably set according to the kind of the treatment agent. Specifically, the temperature is favorably 80° C. or less, more favorably 5° C. or more and 80° C. or less, furthermore favorably 10° C. or more and 70° C. or less, particularly favorably 10° C. or more and 40° C. or less. When the temperature is made high, the reaction rate can be raised. However, side reactions are easy to occur, so that the reaction efficiency may be lowered in some cases. When the temperature is made low on the other hand, the side reactions are hard to occur. However, the reaction rate is lowered, so that the reaction time may become long in some cases.

The production process according to the present invention is generally conducted in a liquid medium. The content (% by mass) of the pigment in the liquid medium is 1.0% by mass or more and 50.0% by mass or less, more favorably 5.0% by mass or more and 40.0% by mass or less based on the total mass of the liquid medium. If the content of the pigment is too high, the viscosity of the reaction system becomes high, which is particularly remarkable in the case where the pigment is carbon black, and so agitation of the reaction system becomes hard, and the reaction efficiency may be thus somewhat lowered in some cases. When the content of the pigment is too low on the other hand, contact frequency between the treatment agent and the pigment in the reaction system is lowered, and so the reaction efficiency may be somewhat lowered in some cases, or turbulent flow is caused by the agitation because the viscosity of the reaction system is too low, and thus agitation efficiency may be liable to decrease in some cases.

The self-dispersible pigment produced can be used in various uses after it is suitably subjected to post treatments such as purification. Specifically, the self-dispersible pigment may be provided as a powdery or pellet-shaped self-dispersible pigment in which no liquid medium is present. In this case, the liquid medium may be removed by pressure reduction or heating making good use of an evaporator. The liquid medium may also be removed by drying making use of a freeze drying process or an oven.

In addition, the self-dispersible pigment may be provided as a dispersion liquid in which the self-dispersible pigment is contained in a liquid medium in a state of being dispersed in the liquid medium. In this case, a dispersion liquid containing the resultant self-dispersible pigment may also be utilized in various uses as it is when only water is used as the liquid medium without using an organic solvent. The self-dispersible pigment may also be provided as a final dispersion liquid after the self-dispersible pigment is subjected to rinsing or adjustment of the content of the self-dispersible pigment. In the case where a liquid medium containing an organic solvent is used, the organic solvent may be removed. Examples of a method of removing the organic solvent include a method in which water is added after the organic solvent is removed by pressure reduction or heating making good use of an evaporator. In addition, there is a method in which a process of adding water after the organic solvent is removed by ultrafiltration is repeated. In particular, when a dispersion liquid in a state where the self-dispersible pigment is dispersed in an aqueous liquid medium is provided, the dispersed state can be retained more stably by ionically dissociating the hydrophilic group contained in the functional group of the self-dispersible pigment. Since the hydrophilic group contained in the functional group is anionic, the dispersion liquid is favorably made alkaline.

The self-dispersible pigment produced is suitable for use as a coloring material in various compositions and articles such as ink, paint, plastic, rubber, paper and carbon fiber.

Pigment Species and Physical Property Values:

As for the pigment constituting the self-dispersible pigment (pigment species), for example, an inorganic pigment such as carbon black, calcium carbonate and titanium oxide, or an organic pigment such as azo, phthalocyanine and quinacridone may be used. Among these, carbon black or the organic pigment is favorably used, and carbon black is particularly favorably used as the pigment because it has more reaction active points on its particle surface than other pigments, and so the introduced amount of the functional group is easy to be increased. As carbon black, any carbon black such as furnace black, lamp black, acetylene black and channel black may be used.

The DBP oil absorption of carbon black is favorably 50 ml/100 g or more and 200 ml/100 g or less, more favorably 120 ml/100 g or more and 170 ml/100 g or less, particularly favorably 120 ml/100 g or more and 150 ml/100 g or less. The DBP oil absorption can be measured by a method conforming to JIS K 6221 or ASTM D 2414. These methods are those in which dibutyl phthalate is added dropwise to 100 g of carbon black under agitation, and then the amount of dibutyl phthalate added is measured at the point of time of the maximum torque.

The specific surface area of carbon black according to the BET method is favorably 100 m$^2$/g or more and 600 m$^2$/g or less. The specific surface area according to the BET method can be measured by a method conforming to JIS K 6217 or ASTM D 6556. These methods are those in which deaerated carbon black is immersed in liquid nitrogen, and then the amount of nitrogen adsorbed on a particle surface of carbon black is measured when having reached the equilibrium.

The primary particle size of carbon black is favorably 10 nm or more and 40 nm or less. Carbon black is generally present in such a state that plural primary particles sterically extend like a bunch of grapes. The primary particle size means a particle size of carbon black (primary particle) of the smallest unit forming one pigment particle. The primary particle size of carbon black can be determined by observing and measuring the particle size of carbon black of the smallest unit forming the pigment particle at about 100 points through a transmission or scanning type electron microscope and calculating the arithmetical mean thereof.

The average particle size of carbon black is favorably 50 nm or more and 200 nm or less. The average particle size means a particle size of carbon black as an ordinarily existing form. In the present invention, the average particle size can be measured as a 50% cumulative value [$D_{50}$ (nm)] in a volume-based particle size distribution by using a dynamic light scattering type particle size distribution measuring device or the like.

The primary particle size of the organic pigment is favorably 50 nm or more and 150 nm or less. In addition, the average particle size of the organic pigment is favorably 50 nm or more and 250 nm or less. The definitions of the primary particle size and average particle size of the organic pigment are the same as the definitions of the primary particle size and average particle size of carbon black, respectively.

Treatment Agent:

In the production process according to the present invention, the compound represented by the general formula (1) is used as the treatment agent. The compound represented by the general formula (1) is a diazene compound substituted with a hydrophilic group. The compound represented by the general formula (1) can be obtained by, for example, removal of a hydrogen atom from the compound represented by the general formula (2). That is, a group represented by $R_1$ can be bonded to a particle surface of a pigment through the compound represented by the general formula (1) by sequential removal of hydrogen atoms from the compound represented by the general formula (2). Therefore, in the present invention, the compound represented by the general formula (2) is also included in the treatment agent used for the treatment of the pigment. The compound represented by the general formula (2) is a compound having a hydrazino group (—NH—NH$_2$) and a hydrophilic group, and so acid-added salts of hydrazines such as hydrazine sulfate and hydrazine hydrochloride are also included therein.

$$HN=N-R_1 \quad (1)$$

$$H_2N-NH-R_1 \quad (2)$$

$R_1$ in the general formulae (1) and (2) is as follows. That is, $R_1$ is a group having at least one of an aliphatic group and an aromatic group and being substituted with at least one hydrophilic group selected from the group consisting of a carboxylic acid group, a sulfonic acid group, a phosphoric acid group and a phosphoric acid group.

As examples of the aliphatic group, there may be mentioned an alkyl group, an alkenyl group and an alkynyl group. The alkyl, alkenyl and alkynyl groups may be any of linear, branched and cyclic chains. The number of carbon atoms in the linear and branched alkyl, alkenyl and alkynyl groups is favorably of about 1 to 12. In addition, the cyclic alkyl, alkenyl and alkynyl groups may be any of a single ring and a complex (fused) ring. The number of elements constituting a ring is favorably about 3 to 8. As examples of the aliphatic group, there may be mentioned linear saturated alkyl groups such as methyl, ethyl, propyl, butyl, pentyl and hexyl groups; branched saturated alkyl groups such as isopropyl, isobutyl and 2-ethylhexyl groups; alkenyl groups such as ethenyl, propenyl and butenyl groups; alkynyl groups such as ethynyl, propynyl and butynyl groups; and alicyclic groups such as cyclopropyl, cyclobutyl, cyclopentyl and cyclohexyl groups. The aliphatic group may have such a substituent as a halogen atom such as a fluorine atom, a chlorine atom and a bromine atom, and a hydroxy group.

As examples of the aromatic group, there may be mentioned an aryl group and a heteroaryl group. The aryl and heteroaryl groups may be any of a single ring and a complex (fused) ring. The number of elements constituting a ring is favorably about 3 to 8. As examples of the aryl group, there may be mentioned a phenyl group, a naphthyl group, an anthracenyl group, a phenanthrenyl group and a biphenyl group. As examples of the heteroaryl group, there may be mentioned a pyridyl group, an imidazolyl group, a pyrazolyl group, a pyridinyl group, a thienyl group and a thiazolyl group. Among these, phenyl, naphthyl, anthracenyl, phenanthrenyl, biphenyl and pyridinyl groups are favorable, and phenyl and naphthyl groups are more favorable.

As examples of the group having at least one of an aliphatic group and an aromatic group, there may be mentioned groups in which the above-mentioned groups are directly or through a general linker structure such as —O—, —NH—, —CO—, —COO—, —CONH—, —N=N—, —SO— and —SO$_2$—. In order to improve the hydrophilicity of the functional group, it is more favorable to let the group having at least one of the aliphatic group and the aromatic group have the linker structure.

The group having at least one of the aliphatic group and the aromatic group will become a linking group (a part thereof) between the particle surface of the pigment and the hydrophilic group. Therefore, the group having at least one of the aliphatic group and the aromatic group may be any group so long as it can modify the pigment into a self-dispersible pigment in relation with the hydrophilic group. That is, if the amount of the hydrophilic group substituted is small although the structure of the linking group is large, the hydrophilicity of the functional group bonded to the particle surface of the pigment does not become high, so that it is difficult to modify the pigment into the self-dispersible pigment. Accordingly, when the structure of the linking group is made large, it is favorable that the amount of the hydrophilic group substituted is made large, or the introduced amount of the functional group at the particle surface of the pigment is increased.

The hydrophilic group with which the group having at least one of the aliphatic group and the aromatic group is substituted is at least one selected from the group consisting of a carboxylic acid group, a sulfonic acid group, a phosphoric acid group and a phosphonic acid group. These hydrophilic groups may also be in the form of a salt or an anhydride so long as it is chemically possible.

The carboxylic acid, sulfonic acid, phosphoric acid and phosphonic acid groups as the hydrophilic groups will be described. When the carboxylic acid, sulfonic acid, phosphoric acid or phosphonic acid group forms a salt, at least one proton of such a group is substituted by a cation. As examples of the cation, there may be mentioned an alkali metal ion, an ammonium ion and an organic ammonium ion. As examples of the alkali metal ion, there may be mentioned lithium, sodium and potassium ions. As examples of the organic ammonium ion, there may be mentioned cations of aliphatic amines such as mono-to tri-alkylamines and aliphatic alcoholamines such as mono - to tri-alkanolamines, and salts thereof. A salt may be present in a state of being dissociated into an ion in an aqueous liquid. However, such a salt is represented as "salt" for convenience's sake.

The substitution number of hydrophilic groups is theoretically equal to the number of hydrogen atoms present in the group having at least one of the aliphatic group and the aromatic group. For example, the substitution number of hydrophilic groups is 1 to 3 for a methyl group, 1 to 5 for an ethyl group, 1 to 5 for a phenyl group, 1 to 7 for a naphthyl group, 1 to 9 for an anthracenyl group and 1 to 4 for a pyridyl group. When one or two hydrophilic groups are actually substituted per one group having at least one of the aliphatic group and the aromatic group though the number may vary according to the structure, the pigment can be modified into the self-dispersible pigment.

$R_1$ becomes a functional group bonded to the particle surface of the pigment. The molecular weight of one functional group is favorably 1,000 or less, more favorably 500 or less. Accordingly, the molecular weight of the moiety of $R_1$ is also favorably 1,000 or less, more favorably 500 or less. In addition, $R_1$ favorably has at least one of a structure containing an arylene group and plural carboxylic acid groups and a structure containing an amide bond and a phosphonic acid group.

Commercially available reagents may also be used as the compounds represented by the general formula (1) and the compounds represented by the general formula (2), which are used as a treatment agent for the pigment. When some one of the compounds is not commercially available, such compound may be synthesized for use. An example of a synthesis process for the treatment agent will now be described. This synthesis process is a process for obtaining a hydrazine compound from an amine compound. Specifically, the description will hereinafter be made taking a case where 4-hydrazinobenzoic acid is synthesized from 4-aminobenzoic acid as an example. Hydroxyamine-o-sulfonic acid is used as a nitrogen source upon addition of nitrogen to the amine compound. The hydrazine compound is formed by causing the amine compound to react with hydroxyamine-o-sulfonic acid under alkaline conditions. When the hydrazine compound is precipitated as a salt (for example, hydrochloride) thereof by adding an acid, the hydrazine compound can be efficiently collected by filtration.

A process for obtaining 2-hydrazino-1-propanol from 2-amino-1-propanol using hydroxylamine-o-sulfonic acid is described in, for example, Journal of the American Chemical Society, 76, 1283-1285 (1954).

Oxidizing Agent:

In the present invention, the step (1) described above may also be conducted in the presence of an oxidizing agent to produce the self-dispersible pigment. The oxidizing agent is used for improving the reaction rate. However, the reaction utilized in the production process according to the present invention can also progress without using the oxidizing agent.

When the oxidizing agent reacts with the pigment, a carbon atom on the particle surface of the pigment is generally oxidized to form a carboxylic acid group. On the other hand, the formation of the compound represented by the general formula (1) from the compound represented by the general formula (2) is promoted by the action of the oxidizing agent in the production process according to the present invention, and so an oxidative radical addition reaction subsequent to this is also promoted. Accordingly, the oxidizing agent does not act directly on the particle surface of the pigment. The reason for this is that the energy necessary for removal of a hydrogen atom from the compounds represented by the general formulae (1) and (2) is smaller than the energy necessary for oxidizing a carbon atom on the particle surface of the pigment to derive a carbonyl species (C=O) (bonding energy between carbon and oxygen). That is, when the compounds represented by the general formulae (1) and (2) are present, the oxidizing agent is considered to be selectively consumed for the removal of the hydrogen atom.

As examples of the oxidizing agent usable in the production process according to the present invention, there may be mentioned halogens, oxoacid compounds, metal oxides, metal halide compounds, metal porphyrin compounds, hexacyanometalate compounds, metal nitrates, hydrogen peroxide and nitric acid.

As examples of the halogens, there may be mentioned chlorine, bromine and iodine. As examples of the oxoacid compounds, there may be mentioned chromic acid, molybdic acid, permanganic acid, vanadic acid, bithmutic acid, hypohalous acid, halous acid, halogen acid and perhalogen acid. These oxoacid compounds may form a salt, but require to have a metal. As examples of a cation forming the salt, there may be mentioned an alkali metal ion and an ammonium ion. The salt may be present in a state of being dissociated into an ion in an aqueous liquid. However, such a salt is represented as "salt" for convenience's sake. As specific examples of the oxoacid compounds, there may be mentioned chromates such as potassium chromate, potassium dichromate, bis(tetrabutylammonium) bichromate, pyridinium bichromate, pyridinium chlorochromate and pyridinium fluorochromate; permanganates such as potassium permanganate, sodium permanganate, ammonium permanganate, silver permanganate, zinc permanganate and magnesium permanganate; vanadates such as ammonium vanadate, potassium vanadate and sodium vanadate; bismuthates such as sodium bismuthate and potassium bismuthate; and hypochlorous acid, chlorous acid, perchloric acid, hypobromous acid, bromous acid, bromic acid, perbromic acid, hypoiodous acid, iodous acid, iodic acid, periodic acid and hypofluorous acid and salts thereof.

As examples of the metal oxides, there may be mentioned manganese oxide, lead oxide, copper oxide, silver oxide and osmium oxide. As examples of the metal halide compounds, there may be mentioned zinc chloride, aluminum chloride, silver chloride, chromium chloride, zirconium chloride, tin chloride, cerium chloride, iron chloride, barium chloride, magnesium chloride and manganese chloride.

As examples of the metal porphyrin compounds, there may be mentioned porphyrin compounds which have a central metal and may be substituted. As specific examples thereof, there may be mentioned tetrabenzoporphyrin compounds, tetraazaporphyrin compounds, phthalocyanine compounds and naphthlocyanine compounds. As examples of the central metal, there may be mentioned Fe, Co, Ni, Cu, Zn, Mg, Pt, Mn, Ru, Cr and Pd. A ligand may be present in the metal, and a publicly known ligand may be used as the ligand.

As examples of the hexacyanometalate compounds, there may be mentioned hexacyanoferrates and hydrates thereof. As specific examples thereof, there may be mentioned potassium hexacyanoferrate, sodium hexacyanoferrate, ammonium hexacyanoferrate, copper hexacyanoferrate, hexacyanoferrate complexes (for example, lithium potassium hexacyanoferrate) and hydrates thereof.

As examples of the metal nitrates, there may be mentioned potassium nitrate, sodium nitrate, silver nitrate and copper nitrate.

For example, organic peroxides, hypervalent iodine compounds and N-oxide compounds may also be used in addition to the oxidizing agents mentioned above.

In addition, an oxidizing agent having a catalytic action may also be used. Among the oxidizing agents mentioned above, the metal halide compounds, metal porphyrin compounds or hexacyanometalate compounds of at least one metal selected from the group consisting of Fe, Co, Ni, Cu, Mg, Mn, Cr and Mo have the catalytic action. The oxidizing agent having the catalytic action can be used again as an oxidizing agent because the oxidizing agent used in the removal of hydrogen atoms becomes a reducing species, and then the reducing species returns to an oxidizing species by the action of oxygen in the reaction system. Accordingly, when the oxidizing agent having the catalytic action is used, the amount of the oxidizing agent used can be reduced. The oxidizing agent having the catalytic action has a metal whose valence is easy to vary (a metal element which can have two or more oxidation states). Specific examples of valence changes of the metal include Fe (II and III), Co (II and III), Ni (II and III), Cu (0, I and II), Mg (0 and II), Mn (II, IV and VII), Cr (II and III) and Mo (IV and V). A mechanism of causing the catalytic action will be described by a specific example. For example, in the case of an oxidizing agent having trivalent iron $Fe^{3+}$ (Fe(III)), which is an oxidizing species, is used in the removal of hydrogen atoms from the hydrazine compound to form $Fe^{2+}$ (Fe(II)), which is reducing species. Thereafter, the reducing species returns to $Fe^{3+}$ (Fe(III)), which is an oxidizing species, by the action of oxygen in the reaction system, whereby the oxidizing species can be used again as the oxidizing agent.

In the production process according to the present invention, the function thereof is not impaired even when the oxidizing agent is used, so that an inert gas such as nitrogen or argon may be utilized because the oxidative radical addition reaction is conducted by removal of hydrogen atoms, not by transfer of oxygen. Examples of a method for introducing the inert gas into the reaction system include a method of causing the gas to flow into the system through a tube from a bomb and a method of causing the gas collected into a balloon to flow into the system through a needle.

Liquid Medium:

The production process according to the present invention is generally conducted in an aqueous liquid medium. As for the aqueous liquid medium, water alone or an aqueous medium which contains water as a main solvent and uses a protonic or aprotic organic solvent in combination may be used. The aqueous medium is a mixed solvent of water and an organic solvent. A solvent which is miscible with or dissolved in water even in any proportion is favorably used as the organic solvent. In particular, a uniformly mixed solvent containing 50% by mass or more of water is favorably used as the aqueous medium. Ion-exchanged water or pure water is favorably used as the water.

The protonic organic solvent is an organic solvent having a hydrogen atom bonded to oxygen or nitrogen (an acidic hydrogen atom). The aprotic organic solvent is an organic solvent having no acidic hydrogen atom. As examples of the organic solvent, there may be mentioned alcohols, alkylene glycols, polyalkylene glycols, glycol ethers, glycol ether esters, carboxylic acid amides, ketones, keto-alcohols, cyclic ethers, nitrogen-containing compounds and sulfur-containing compounds.

As examples of the liquid medium suitably usable in the production process according to the present invention, there may be mentioned water, water/methanol mixed solvents, water/ethanol mixed solvents, water/ethylene glycol mixed solvents, water/N-methylpyrrolidone mixed solvents, water/tetrahydrofuran mixed solvent and water/acetone mixed solvents.

Ink:

Self-Dispersible Pigment:

The ink according to the present invention contains a self-dispersible pigment as a coloring material. This self-dispersible pigment is the self-dispersible pigment produced by the above-described production process according to the present invention. The self-dispersible pigment is used as the coloring material, so that addition of a dispersant for dispersing a pigment in an ink is unnecessary. Alternatively, the amount of the dispersant added can be reduced. The content (% by mass) of the self-dispersible pigment in the ink is favorably 0.1% by mass or more and 15.0% by mass or less, more favorably 1.0% by mass or more and 10.0% by mass or less based on the total mass of the ink. The ink according to the present invention may contain a dye together with the pigment for the purpose of color adjustment.

In the self-dispersible pigment used as the coloring material in the ink according to the present invention, a hydrophilic group is contained in the functional group thereof. When the ink according to the present invention is an aqueous ink, the introduced amount of the functional group into the pigment is favorably 0.10 mmol/g or more. If the introduced amount of the functional group into the pigment is less than 0.10 mmol/g, the dispersion stability may be somewhat lowered. In addition, the introduced amount of the functional group into the pigment is favorably 1.00 mmol/g or less, more favorably 0.80 mmol/g or less.

The introduced amount of the functional group is an index indicating the amount of the functional group bonded directly or through another atomic group to the particle surface of the pigment and represented by an amount (mmol) of the functional group per 1 g of the self-dispersible pigment. In the present invention, the introduced amount of the functional group is determined in the following manner. First, the structure of the functional group is identified by simultaneous differential thermal balance mass analysis (TG-MS) or solid state NMR. The introduced amount of the hydrophilic group is then determined by a colloid titration method. Methyl glycol chitosan or hydrochloric acid may be used in the analysis of the hydrophilic group by the colloid titration method. Thereafter, the introduced amount of the hydrophilic group is divided by the number of hydrophilic groups when plural hydrophilic groups are contained in one functional group to convert it to the introduced amount (mmol) of the functional group per 1 g of the self-dispersible pigment.

Aqueous Medium:

In the ink according to the present invention, water or an aqueous medium which is a mixed solvent of water and a water-soluble organic solvent may be used. In the present invention, an aqueous ink containing at least water as an aqueous medium is favorably provided. Deionized water (ion-exchanged water) is favorably used as the water. The content (% by mass) of water in the ink is favorably 10.0% by mass or more and 90.0% by mass or less, more favorably 50.0% by mass or more and 90.0% by mass or less based on the total mass of the ink.

No particular limitation is imposed on the water-soluble organic solvent so long as it is soluble in water, and then an alcohol, a polyhydric alcohol, a polyglycol, a nitrogen-containing polar solvent or a sulfur-containing polar solvent may be used. Among these, a water-soluble organic solvent having a lower vapor pressure at 25° C. than water is favorably used. The content (% by mass) of the water-soluble organic solvent in the ink is favorably 5.0% by mass or more and 90.0% by mass or less, more favorably 10.0% by mass or more and 50.0% by mass or less based on the total mass of the ink.

Other Additives:

The ink according to the present invention may also contain a water-soluble organic compound which is solid at ordinary temperature, such as a polyhydric alcohol such as trimethylolpropane and trimethylolethane, urea, a urea derivative such as ethyleneurea and hydantoin, or a sugar, as needed, in addition to the above-described components. In addition, the ink according to the present invention may also contain various additives such as a surfactant, a pH adjustor, a rust preventive, a preservative, a mildewproofing agent, an antioxidant, an antireductant, an evaporation accelerating agent, a chelating agent and a water-soluble resin, as needed.

Examples of the surfactant include anionic, cationic and nonionic surfactants. The content (% by mass) of the surfactant in the ink is favorably 0.1% by mass or more and 5.0% by mass or less, more favorably 0.1% by mass or more and 2.0% by mass or less based on the total mass of the ink.

A nonionic surfactant such as a polyoxyethylene alkyl ether, a polyoxyethylene fatty acid ester, a polyoxyethylene alkyl phenyl ether, a polyoxyethylene-polyoxypropylene block copolymer or an acetylene glycol-based compound is favorably used as the surfactant. The hydrophobic group of the surfactant is easy to adsorb on the particle surface of the self-dispersible pigment. Thus, the dispersed state of the self-dispersible pigment in the ink can be more stably retained. The reason for this is as follows. Among the surfactants, the nonionic surfactant has no ionic group, so that its interaction with the functional group of the self-dispersible pigment is hard to occur, but it is easy to adsorb on the particle surface of the self-dispersible pigment.

Physical Properties of Ink:

In the case where the ink according to the present invention is applied to an ink jet system, it is favorable to suitably control the physical property values thereof. Specifically, the surface tension of the ink at 25° C. is favorably 10 mN/m or more and 60 mN/m or less, more favorably 20 mN/m or more and 60 mN/m or less. In particular, the surface tension is favorably 30 mN/m or more and 50 mN/m or less, more favorably 30 mN/m or more and 40 mN/m or less. The viscosity of the ink at 25° C. is favorably 1.0 mP·s or more and 10.0 mP·s or less, more favorably 1.0 mP·s or more and 5.0 mP·s or less, particularly favorably 1.0 mP·s or more and 3.0 mP·s or less. The pH of the ink at 25° C. is favorably 5 or more and 9 or less.

Figure 4:
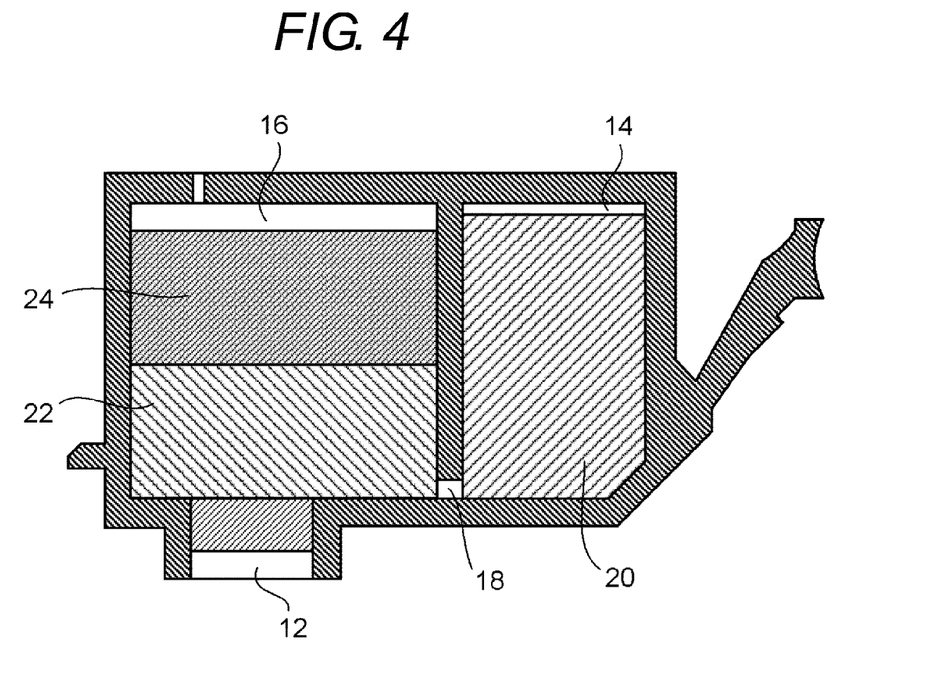
FIG. 4 is a sectional view schematically illustrating an ink cartridge according to an embodiment of the present invention.

Ink Cartridge:

The ink cartridge according to the present invention is provided with an ink and an ink storage portion storing this ink. The ink stored in this ink storage portion is the above-described ink according to the present invention. FIG. 4 is a sectional view schematically illustrating an ink cartridge according to an embodiment of the present invention. As illustrated in FIG. 4, an ink supply port 12 for supplying the ink to a recording head is provided in a bottom surface of the ink cartridge. The interior of the ink cartridge is the ink storage portion for storing the ink. The ink storage portion is constituted by an ink storage chamber 14 and an absorber storage chamber 16, and these chambers are communicated with each other through a communication port 18. The absorber storage chamber 16 is communicated with the ink supply port 12. A liquid ink 20 is stored in the ink storage chamber 14, and absorbers 22 and 24 holding the ink in an impregnated state are stored in the absorber storage chamber 16. The ink storage portion may also be so constructed that the whole amount of the ink stored is held by the absorber without providing the ink storage chamber storing the liquid ink. In addition, the ink storage portion may also be so constructed that the whole amount of the ink is stored in a liquid state without having the absorber. Further, the ink cartridge may also be constructed so as to have an ink storage portion and a recording head.

Ink Jet Recording Method:

The ink jet recording method according to the present invention is a method of ejecting the above-described ink according to the present invention from a recording head of an ink jet system to record an image on a recording medium. As systems for ejecting the ink, a system in which mechanical energy is applied to the ink and a system in which thermal energy is applied to the ink are mentioned. In the present invention, the system in which the thermal energy is applied to the ink to eject the ink is particularly favorably adopted. Steps of the ink jet recording method may be those publicly known except that the ink according to the present invention is used.

Figure 5A:
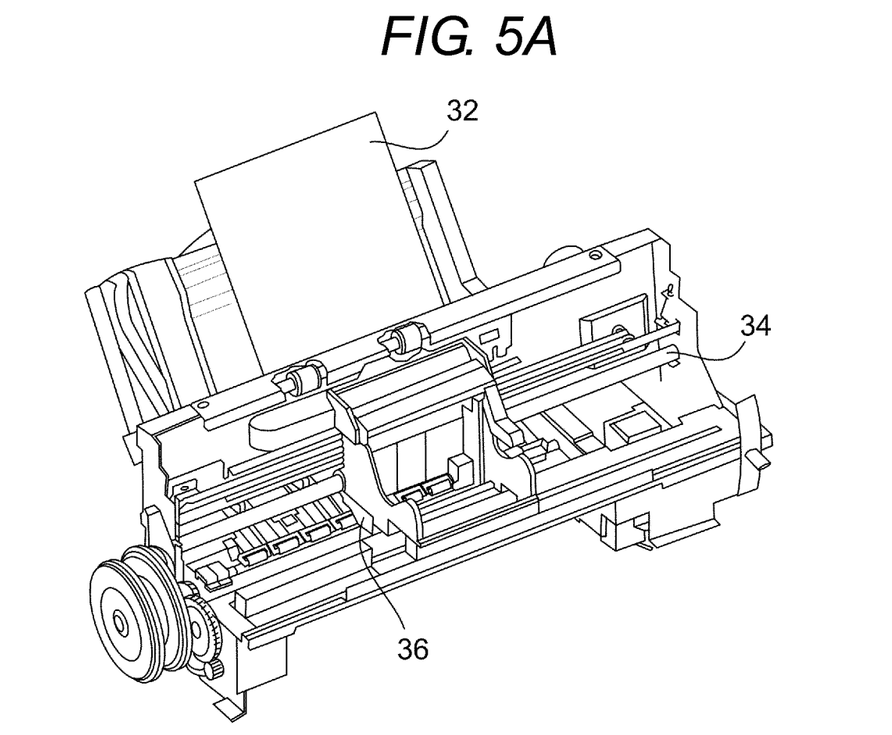
FIG. 5A is a perspective view illustrating a principal part of the ink jet recording apparatus.
Figure 5B:
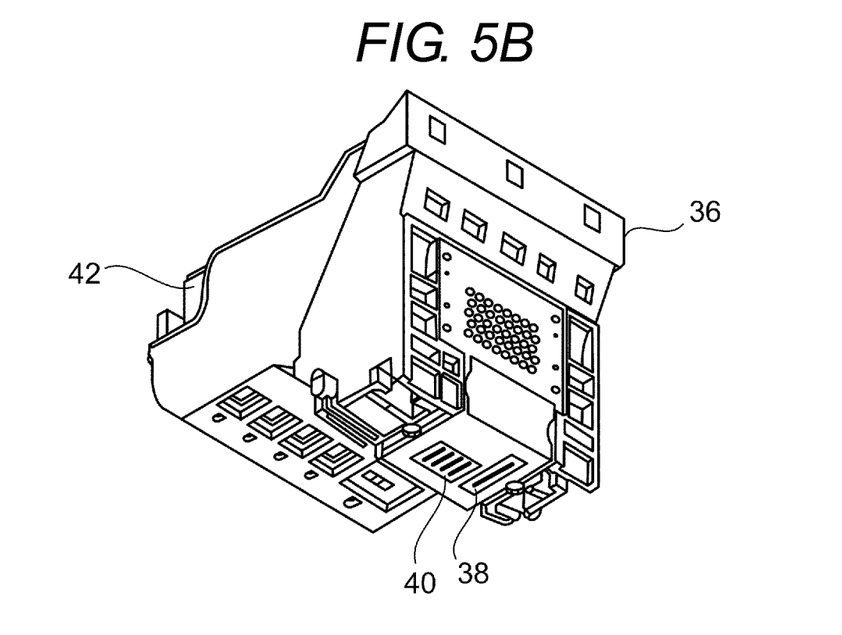
FIG. 5B is a perspective view illustrating a head cartridge.

FIGS. 5A and 5B schematically illustrate an example of an ink jet recording apparatus used in the ink jet recording method according to the present invention, in which FIG. 5A is a perspective view illustrating a principal part of the ink jet recording apparatus, and FIG. 5B is a perspective view illustrating a head cartridge. In the ink jet recording apparatus, a conveyance unit (not illustrated) for conveying a recording medium 32 and a carriage shaft 34 are provided. A head cartridge 36 can be mounted on the carriage shaft 34. The head cartridge 36 is provided with recording heads 38 and 40 and is so constructed that an ink cartridge 42 is set. Inks (not illustrated) are ejected toward the recording medium 32 from the recording heads 38 and 40 while the head cartridge 36 is being carried in a primary scanning direction along the carriage shaft 34. The recording medium 32 is then conveyed in a secondary scanning direction by the conveyance unit (not illustrated), whereby an image is recorded on the recording medium 32.

EXAMPLES

The present invention will hereinafter be described in more detail by the following Examples and Comparative Examples. However, the present invention is not limited by the following examples unless going beyond the gist of the present invention. Incidentally, all designations of "part" or "parts" and "%" as to amounts of components are based on mass unless expressly noted.

Analytical Conditions:

A small amount of a sample was taken out in the middle of a reaction of producing a self-dispersible pigment, and then the pigment was removed to obtain a separate liquid. Qualitative analysis of components contained in the separate liquid was performed by a liquid chromatography mass spectrometry (LCMS) method using an LC/MSD TOF apparatus (manufactured by Agilent) to estimate radical species formed during the reaction. By this analysis, the reaction mechanism can be estimated, and whether the reaction produces a small amount of byproducts or not can be known.

Production of Self-Dispersible Pigment:

In the following description as to a production process, "mmol/g" means the number of millimoles (mmol) per 1.0 g of a pigment. Those available from Sumika Technoservice Corporation are used as treatment agents.

Example 1

Figure 1:
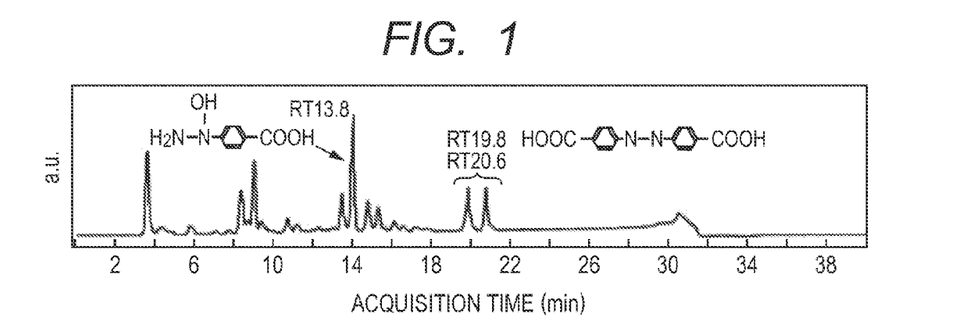
FIG. 1 illustrates an LCMS analysis result (chart) of a separate liquid obtained in the process of production of Self-Dispersible Pigment 1.

18.0 grams of a pigment, 180 ml of ion-exchanged water and 1.0 mmol/g of a treatment agent were placed in a vessel (manufactured by IMEX Co., Ltd.) having a capacity of 400 ml and mixed. Carbon black (trade name "TOKA BLACK #8300", product of Tokai Carbon Co., Ltd.) was used as the pigment. 4-Hydrazinobenzoic acid was used as the treatment agent. After the pH of the resultant liquid was adjusted to 9 by adding 15 ml of a 5 mol/l aqueous solution of sodium hydroxide, the liquid was agitated for 12 hours at 25° C. and the number of revolutions of 2,000 rpm to obtain a dispersion liquid. The dispersion liquid was purified by removing impurities from the dispersion liquid by using an ultrafilter (trade name "RP-2100", manufactured by Aira Co.; filter: pencil-shaped module "SAP-0013", manufactured by Asahi Kasei Chemicals Corporation). The purification was conducted by repeating a process of concentrating the dispersion liquid to 50 ml by the ultrafilter (150 ml of the filtrate fractionated) and then adding 150 ml of ion-exchanged water to dilute the dispersion liquid until the electrical conductivity of the filtrate reached 50 µS/cm or lower. After the content of the resultant self-dispersible pigment was controlled by ultrafiltration, the resultant dispersion liquid was centrifuged at a number of revolutions of 5,000 rpm to remove coarse particles, thereby obtaining an aqueous dispersion liquid of Self-Dispersible Pigment 1, in which the content of Self-Dispersible Pigment 1 was 10.0%. An LCMS analysis result (chart) of a separate liquid obtained in the process of the production of Self-Dispersible Pigment 1 is illustrated in FIG. 1. FIG. 1 illustrates a result (chart) obtained by the LCMS analysis of the separate liquid when the treatment agent has just disappeared. Structural formulae in FIG. 1 were estimated from mass spectra obtained by the mass spectrometry.

Example 2

An aqueous dispersion liquid of Self-Dispersible Pigment 2 was obtained in the same manner as in Example 1 except that the treatment agent was changed to 4-hydrazinophthalic acid hydrochloride.

Example 3

An aqueous dispersion liquid of Self-Dispersible Pigment 3 was obtained in the same manner as in Example 1 except that the treatment agent was changed to 5-hydrazinosalicylic acid hydrochloride.

Example 4

An aqueous dispersion liquid of Self-Dispersible Pigment 4 was obtained in the same manner as in Example 1 except that the treatment agent was changed to 5 hydrazinobenzenesulfonic acid.

Example 5

An aqueous dispersion liquid of Self-Dispersible Pigment 5 was obtained in the same manner as in Example 1 except that the treatment agent was changed to p-(4-hydrazinylphenyl)phosphonic acid.

Example 6

An aqueous dispersion liquid of Self-Dispersible Pigment 6 was obtained in the same manner as in Example 1 except that the treatment agent was changed to a mixture of 0.5 mmol/g of 4-hydrazinobenzoic acid and 0.5 mmol/g of 4-hydrazinobenzenesulfonic acid.

Example 7

An aqueous dispersion liquid of Self-Dispersible Pigment 7 was obtained in the same manner as in Example 1 except that the treatment agent was changed to a mixture of 0.5 mmol/g of 4-hydrazinobenzoic acid and 0.5 mmol/g of p-(4-hydrazinylphenyl)phosphonic acid.

Example 8

An aqueous dispersion liquid of Self-Dispersible Pigment 8 was obtained in the same manner as in Example 1 except that the treatment agent was changed to P,P'-[[(4-hydrazinobenzyl)amino]methylene]bisphosphonic acid hydrochloride.

Example 9

An aqueous dispersion liquid of Self-Dispersible Pigment 9 was obtained in the same manner as in Example 1 except that the treatment agent was changed to (4-hydrazinophenyl) acetic acid hydrochloride.

Example 10

An aqueous dispersion liquid of Self-Dispersible Pigment 10 was obtained in the same manner as in Example 1 except that the treatment agent was changed to 4-hydrazinophenoxyacetic acid hydrochloride.

Example 11

An aqueous dispersion liquid of Self-Dispersible Pigment 11 was obtained in the same manner as in Example 1 except that the treatment agent was changed to 3-(4-hydrazinophenyl)tartaric acid hydrochloride.

Example 12

An aqueous dispersion liquid of Self-Dispersible Pigment 12 was obtained in the same manner as in Example 1 except that the oxidizing agent was changed to 0.1 mmol/g of iron (III) chloride.

Example 13

An aqueous dispersion liquid of Self-Dispersible Pigment 13 was obtained in the same manner as in Example 1 except that the oxidizing agent was changed to 0.1 mmol/g of sodium periodate.

Example 14

An aqueous dispersion liquid of Self-Dispersible Pigment 14 was obtained in the same manner as in Example 1 except that the 5 mol/l aqueous solution of sodium hydroxide was changed to 30 ml of 28% aqueous ammonia.

Example 15

An aqueous dispersion liquid of Self-Dispersible Pigment 15 was obtained in the same manner as in Example 1 except that the temperature upon the reaction was changed to 80° C., the vessel was changed to a 500-ml three-necked flask with a reflux condenser, and the number of revolutions was changed to 300 rpm.

Example 16

An aqueous dispersion liquid of Self-Dispersible Pigment 16 was obtained in the same manner as in Example 1 except that the temperature upon the reaction was changed to 85° C., the vessel was changed to a 500-ml three-necked flask with a reflux condenser, and the number of revolutions was changed to 300 rpm.

Example 17

An aqueous dispersion liquid of Self-Dispersible Pigment 17 was obtained in the same manner as in Example 1 except that the pigment was changed to carbon black (trade name "NIPEX 170IQ", product of Orion Engineered Carbons).

Example 18

An aqueous dispersion liquid of Self-Dispersible Pigment 18 was obtained in the same manner as in Example 1 except that the pigment was changed to carbon black (trade name "#2600", product of Mitsubishi Chemical Corporation).

Example 19

An aqueous dispersion liquid of Self-Dispersible Pigment 19 was obtained in the same manner as in Example 1 except that the treatment agent was changed to 4-hydrazinophthalic acid hydrochloride, and 0.1 mmol/g of potassium ferrocyanide (trihydrate) was used as the oxidizing agent.

Example 20

An aqueous dispersion liquid of Self-Dispersible Pigment 20 was obtained in the same manner as in Example 1 except that the treatment agent was changed to 4-hydrazinophthalic acid hydrochloride, and 0.1 mmol/g of iodine was used as the oxidizing agent.

Example 21

An aqueous dispersion liquid of Self-Dispersible Pigment 21 was obtained in the same manner as in Example 1 except that the treatment agent was changed to 4-hydrazinophthalic acid hydrochloride, and 0.1 mmol/g of iron(III) chloride was used as the oxidizing agent.

Example 22

An aqueous dispersion liquid of Self-Dispersible Pigment 22 was obtained in the same manner as in Example 1 except that the treatment agent was changed to 4-hydrazinophthalic acid hydrochloride, and 0.1 mmol/g of sodium periodate was used as the oxidizing agent.

Example 23

An aqueous dispersion liquid of Self-Dispersible Pigment 23 was obtained in the same manner as in Example 1 except that the treatment agent was changed to 4-hydrazinophthalic acid hydrochloride, and 0.1 mmol/g of potassium permanganate was used as the oxidizing agent.

Example 24

An aqueous dispersion liquid of Self-Dispersible Pigment 24 was obtained in the same manner as in Example 1 except that the treatment agent was changed to 4-hydrazinophthalic acid hydrochloride, and 0.1 mmol/g of hydrogen peroxide (35% aqueous solution) was used as the oxidizing agent.

Example 25

An aqueous dispersion liquid of Self-Dispersible Pigment 25 was obtained in the same manner as in Example 1 except that the treatment agent was changed to 4-hydrazinophthalic acid hydrochloride, and the agitation time was changed to 96 hours.

Example 26

An aqueous dispersion liquid of Self-Dispersible Pigment 26 was obtained in the same manner as in Example 1 except that the treatment agent was changed to 4-hydrazinophthalic acid hydrochloride, and the 5 mol/l aqueous solution of sodium hydroxide was changed to 30 ml of 28% aqueous ammonia.

Example 27

An aqueous dispersion liquid of Self-Dispersible Pigment 27 was obtained in the same manner as in Example 1 except that the treatment agent was changed to 4-hydrazinophthalic acid hydrochloride, the temperature upon the reaction was changed to 80° C., the vessel was changed to a 500-ml three-necked flask with a reflux condenser, and the number of revolutions was changed to 300 rpm.

Example 28

An aqueous dispersion liquid of Self-Dispersible Pigment 28 was obtained in the same manner as in Example 1 except that the treatment agent was changed to 4-hydrazinophthalic acid hydrochloride, the temperature upon the reaction was changed to 85° C., the vessel was changed to a 500-ml three-necked flask with a reflux condenser, and the number of revolutions was changed to 300 rpm.

Example 29

An aqueous dispersion liquid of Self-Dispersible Pigment 29 was obtained in the same manner as in Example 1 except that the treatment agent was changed to 4-hydrazinophthalic acid hydrochloride, and the pigment was changed to carbon black (trade name "NIPEX 170IQ", product of Orion Engineered Carbons).

Example 30

An aqueous dispersion liquid of Self-Dispersible Pigment 30 was obtained in the same manner as in Example 1 except that the treatment agent was changed to 4-hydrazinophthalic acid hydrochloride, and the pigment was changed to carbon black (trade name "#2600", product of Mitsubishi Chemical Corporation).

Example 31

An aqueous dispersion liquid of Self-Dispersible Pigment 31 was obtained in the same manner as in Example 1 except that the treatment agent was changed to 4-hydrazinophthalic acid hydrochloride, and the pigment was changed to carbon black (trade name "MCF88", product of Mitsubishi Chemical Corporation).

Example 32

An aqueous dispersion liquid of Self-Dispersible Pigment 32 was obtained in the same manner as in Example 1 except that the treatment agent was changed to 4-hydrazinophthalic acid hydrochloride, and the pigment was changed to Color Black FW200 (product of Orion Engineered Carbons).

Example 33

An aqueous dispersion liquid of Self-Dispersible Pigment 33 was obtained in the same manner as in Example 1 except that the treatment agent was changed to 4-hydrazinophthalic acid hydrochloride, and the pigment was changed to C.I. Pigment Blue 15:3 (trade name "Heliogen Blue D 7079", product of BASF).

Example 34

An aqueous dispersion liquid of Self-Dispersible Pigment 34 was obtained in the same manner as in Example 1 except that the treatment agent was changed to 4-hydrazinophthalic acid hydrochloride, and the pigment was changed to C.I. Pigment Red 122 (trade name "Hostaperm Pink E02", product of Clariant).

Example 35

An aqueous dispersion liquid of Self-Dispersible Pigment 35 was obtained in the same manner as in Example 1 except that the treatment agent was changed to 4-hydrazinophthalic acid hydrochloride, and the pigment was changed to C.I. Pigment Yellow 155 (trade name "Inkjet Yellow 4G", product of Clariant).

Example 36

An aqueous dispersion liquid of Self-Dispersible Pigment 36 was obtained in the same manner as in Example 1 except that the treatment agent was changed to P,P'-[[(4-hydrazinobenzyl)amino]methylene]bisphosphonic acid hydrochloride, and 0.1 mmol/g of iron(III) chloride was used as the oxidizing agent.

Example 37

An aqueous dispersion liquid of Self-Dispersible Pigment 37 was obtained in the same manner as in Example 1 except that the treatment agent was changed to P,P'-[[(4-hydrazinobenzyl)amino]methylene]bisphosphonic acid hydrochloride, and 0.1 mmol/g of sodium periodate was used as the oxidizing agent.

Example 38

An aqueous dispersion liquid of Self-Dispersible Pigment 38 was obtained in the same manner as in Example 1 except that the treatment agent was changed to P,P'-[[(4-hydrazinobenzyl)amino]methylene]bisphosphonic acid hydrochloride, and the 5 mol/l aqueous solution of sodium hydroxide was changed to 30 ml of 28% aqueous ammonia.

Example 39

An aqueous dispersion liquid of Self-Dispersible Pigment 39 was obtained in the same manner as in Example 1 except that the treatment agent was changed to P,P'-[[(4-hydrazinobenzyl)amino]methylene]bisphosphonic acid hydrochloride, the temperature upon the reaction was changed to 80° C., the vessel was changed to a 500-ml three-necked flask with a reflux condenser, and the number of revolutions was changed to 300 rpm.

Example 40

An aqueous dispersion liquid of Self-Dispersible Pigment 40 was obtained in the same manner as in Example 1 except that the treatment agent was changed to P,P'-[[(4-hydrazinobenzyl)amino]methylene]bisphosphonic acid hydrochloride, the temperature upon the reaction was changed to 85° C., the vessel was changed to a 500-ml three-necked flask with a reflux condenser, and the number of revolutions was changed to 300 rpm.

Example 41

An aqueous dispersion liquid of Self-Dispersible Pigment 41 was obtained in the same manner as in Example 1 except that the treatment agent was changed to P,P'-[[(4-hydrazinobenzyl)amino]methylene]bisphosphonic acid hydrochloride, and the pigment was changed to carbon black (trade name "NIPEX 170IQ", product of Orion Engineered Carbons).

Example 42

An aqueous dispersion liquid of Self-Dispersible Pigment 42 was obtained in the same manner as in Example 1 except that the treatment agent was changed to P,P'-[[(4-hydrazinobenzyl)amino]methylene]bisphosphonic acid hydrochloride, and the pigment was changed to carbon black (trade name "#2600", product of Mitsubishi Chemical Corporation).

Comparative Example 1

Figure 2:
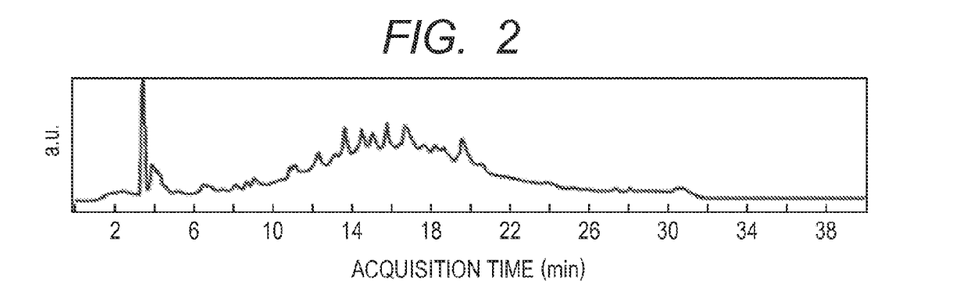
FIG. 2 illustrates an LCMS analysis result (chart) of a separate liquid obtained in the process of production of Comparative Self-Dispersible Pigment 1.

An aqueous dispersion liquid of Comparative Self-Dispersible Pigment 1 was obtained according to the following procedure conforming to the description in Japanese Patent Application Laid-Open No. H10-510861. Into a 300-ml flask, 3.0 mmol/g of p-aminobenzoic acid (product of TOKYO CHEMICAL INDUSTRY CO., LTD.) and 25 ml of ion-exchanged water were put, and the temperature of the contents was kept at 5° C. by an ice bath. After 5 ml of concentrated hydrochloric acid was additionally added, a solution with 1.5 g of sodium nitrite (product of TOKYO CHEMICAL INDUSTRY CO., LTD.) dissolved in 5.4 ml of ion-exchanged water was added dropwise, and the resultant mixture was agitated for 2 hours while keeping the temperature to obtain a liquid product. After 18.0 g of a pigment and 200 ml of ion-exchanged water were put in a vessel (manufactured by IMEX Co., Ltd.) having a capacity of 400 ml, the liquid product obtained above was added, and the resultant mixture was agitated for 12 hours at 25° C. and a number of revolutions of 2,000 rpm. Carbon black (trade name "TOKA BLACK #8300" product of Tokai Carbon Co., Ltd.) was used as the pigment. Thereafter, the pH of the liquid was adjusted to 9 by adding 15 ml of a 5 mol/l aqueous solution of sodium hydroxide. Purification was then conducted in the same manner as in Example 1 to obtain an aqueous dispersion liquid of Comparative Self-Dispersible Pigment 1, in which the content of Comparative Self-Dispersible Pigment 1 was 10.0%. An LCMS analysis result (chart) of a separate liquid obtained in the process of the production of Comparative Self-Dispersible Pigment 1 is illustrated in FIG. 2. FIG. 2 illustrates a result (chart) obtained by the LCMS analysis of the separate liquid when the treatment agent has just disappeared.

Comparative Example 2

Figure 3:
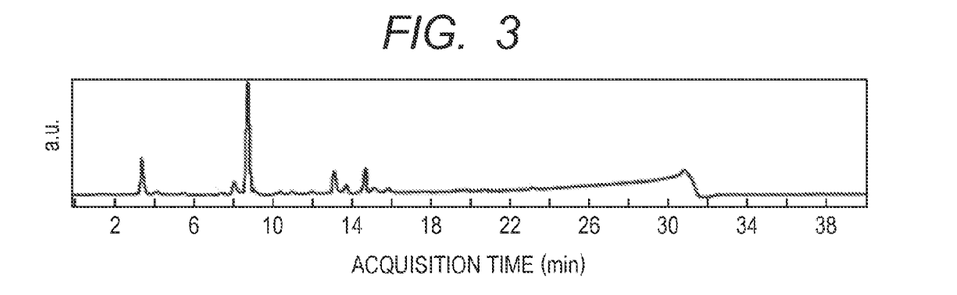
FIG. 3 illustrates an LCMS analysis result (chart) of a separate liquid obtained in the process of production of Comparative Self-Dispersible Pigment 2.

An aqueous dispersion liquid of Comparative Self-Dispersible Pigment 2 was obtained according to the following procedure conforming to the description in Japanese Patent Application Laid-Open No. 2012-528917. Eighteen grams of a pigment, 200 ml of ion-exchanged water and 1.0 mmol/g of 4-hydrazinobenzoic acid (product of TOKYO CHEMICAL INDUSTRY CO., LTD.) were mixed, and the pH of the resultant liquid was adjusted to 9 with ammonium hydroxide to obtain a liquid mixture. Carbon black (trade name "TOKA BLACK #8300" product of Tokai Carbon Co., Ltd.) was used as the pigment. The resultant liquid mixture was put in a Pyrex (trademark) dish, and the dish was put into an oven and heated for 24 hours at a temperature of 120° C. to dry the pigment to solids. The dried pigment was dispersed in ion-exchanged water, and the resultant dispersion liquid was subjected to ultrasonication. Purification was then conducted in the same manner as in Example 1 to obtain an aqueous dispersion liquid of Comparative Self-Dispersible Pigment 2, in which the content of Comparative Self-Dispersible Pigment 2 was 10.0%. An LCMS analysis result (chart) of a separate liquid obtained in the process of the production of Comparative Self-Dispersible Pigment 2 is illustrated in FIG. 3. FIG. 3 illustrates a result (chart) obtained by the LCMS analysis of the separate liquid when the treatment agent has just disappeared.

Comparative Example 3

An aqueous dispersion liquid of Comparative Self-Dispersible Pigment 3 was obtained in the same manner as in Comparative Example 1 except that the temperature upon the reaction was changed to 80° C.

Conditions for Production of Self-Dispersible Pigment:

Conditions for production of a self-dispersible pigment are shown in Table 1. Meanings (kinds of pigments) of abbreviations in Table 1 are as follows.

CB1: TOKA BLACK #8300 (product of Tokai Carbon Co., Ltd.)

CB2: NIPEX 170IQ (product of Orion Engineered Carbons)

CB3: #2600 (product of Mitsubishi Chemical Corporation)

CB4: MCF88 (product of Mitsubishi Chemical Corporation)

CB5: Color Black FW200 (product of Orion Engineered Carbons)

PC: Heliogen Blue D 7079 (product of BASF)

QA: Hostaperm Pink E02 (product of Clariant)

AZ: Inkjet Yellow 4G (product of Clariant).

TABLE 1

Conditions for production of self-dispersible pigment

| | Kind of pigment | Treatment agent | Oxidizing agent | Reaction conditions pH | Temp (° C.) | Agitation time (hr) |
|---|---|---|---|---|---|---|
| Ex. 1 | CB1 | 4-Hydrazinobenzoic acid | — | 9 | 25 | 12 |
| Ex. 2 | CB1 | 4-Hydrazinophthalic acid hydrochloride | — | 9 | 25 | 12 |
| Ex. 3 | CB1 | 5-Hydrazinosalicylic acid hydrochloride | — | 9 | 25 | 12 |
| Ex. 4 | CB1 | 4-Hydrazinobenzenesulfonic acid | — | 9 | 25 | 12 |
| Ex. 5 | CB1 | p-(4-Hydrazinylphenyl)phosphonic acid | — | 9 | 25 | 12 |
| Ex. 6 | CB1 | 4-Hydrazinobenzoic acid 4-Hydrazinobenzenesulfonic acid | — | 9 | 25 | 12 |
| Ex. 7 | CB1 | 4-Hydrazinobenzoic acid p-(4-Hydrazinylphenyl)phosphonic acid | — | 9 | 25 | 12 |
| Ex. 8 | CB1 | P,P'-[[(4-Hydrazinobenzyl)amino]methylene] bisphosphonic acid hydrochloride | — | 9 | 25 | 12 |
| Ex. 9 | CB1 | 4-Hydrazinophenylacetic acid hydrochloride | — | 9 | 25 | 12 |
| Ex. 10 | CB1 | 4-Hydrazinophenoxyacetic acid hydrochloride | — | 9 | 25 | 12 |
| Ex. 11 | CB1 | 3-(4-Hydrazinophenyl)tartaric acid hydrochloride | — | 9 | 25 | 12 |
| Ex. 12 | CB1 | 4-Hydrazinobenzoic acid | $FeCl_3$ | 9 | 25 | 12 |
| Ex. 13 | CB1 | 4-Hydrazinobenzoic acid | $NaIO_4$ | 9 | 25 | 12 |
| Ex. 14 | CB1 | 4-Hydrazinobenzoic acid | — | 9 | 25 | 12 |
| Ex. 15 | CB1 | 4-Hydrazinobenzoic acid | — | 9 | 80 | 12 |
| Ex. 16 | CB1 | 4-Hydrazinobenzoic acid | — | 9 | 85 | 12 |
| Ex. 17 | CB2 | 4-Hydrazinobenzoic acid | — | 9 | 25 | 12 |
| Ex. 18 | CB3 | 4-Hydrazinobenzoic acid | — | 9 | 25 | 12 |
| Ex. 19 | CB1 | 4-Hydrazinophthalic acid hydrochloride | $K_4[Fe(CN)_6] \cdot 3H_2O$ | 9 | 25 | 12 |
| Ex. 20 | CB1 | 4-Hydrazinophthalic acid hydrochloride | $I_2$ | 9 | 25 | 12 |
| Ex. 21 | CB1 | 4-Hydrazinophthalic acid hydrochloride | $FeCl_3$ | 9 | 25 | 12 |
| Ex. 22 | CB1 | 4-Hydrazinophthalic acid hydrochloride | $NaIO_4$ | 9 | 25 | 12 |
| Ex. 23 | CB1 | 4-Hydrazinophthalic acid hydrochloride | $KMnO_4(H_2SO_4\text{-acidified})$ | 2 | 25 | 12 |
| Ex. 24 | CB1 | 4-Hydrazinophthalic acid hydrochloride | $H_2O_2(H_2SO_4\text{-acidified})$ | 2 | 25 | 12 |
| Ex. 25 | CB1 | 4-Hydrazinophthalic acid hydrochloride | — | 9 | 25 | 96 |
| Ex. 26 | CB1 | 4-Hydrazinophthalic acid hydrochloride | — | 9 | 25 | 12 |
| Ex. 27 | CB1 | 4-Hydrazinophthalic acid hydrochloride | — | 9 | 80 | 12 |
| Ex. 28 | CB1 | 4-Hydrazinophthalic acid hydrochloride | — | 9 | 85 | 12 |
| Ex. 29 | CB2 | 4-Hydrazinophthalic acid hydrochloride | — | 9 | 25 | 12 |
| Ex. 30 | CB3 | 4-Hydrazinophthalic acid hydrochloride | — | 9 | 25 | 12 |
| Ex. 31 | CB4 | 4-Hydrazinophthalic acid hydrochloride | — | 9 | 25 | 12 |
| Ex. 32 | CB5 | 4-Hydrazinophthalic acid hydrochloride | — | 9 | 25 | 12 |
| Ex. 33 | PC | 4-Hydrazinophthalic acid hydrochloride | — | 9 | 25 | 12 |
| Ex. 34 | QA | 4-Hydrazinophthalic acid hydrochloride | — | 9 | 25 | 12 |
| Ex. 35 | AZ | 4-Hydrazinophthalic acid hydrochloride | — | 9 | 25 | 12 |
| Ex. 36 | CB1 | P,P'-[[(4-Hydrazinobenzyl)amino]methylene] bisphosphonic acid hydrochloride | $FeCl_3$ | 9 | 25 | 12 |
| Ex. 37 | CB1 | P,P'-[[(4-Hydrazinobenzyl)amino]methylene] bisphosphonic acid hydrochloride | $NaIO_4$ | 9 | 25 | 12 |
| Ex. 38 | CB1 | P,P'-[[(4-Hydrazinobenzyl)amino]methylene] bisphosphonic acid hydrochloride | — | 9 | 25 | 12 |
| Ex. 39 | CB1 | P,P'-[[(4-Hydrazinobenzyl)amino]methylene] bisphosphonic acid hydrochloride | — | 9 | 80 | 12 |
| Ex. 40 | CB1 | P,P'-[[(4-Hydrazinobenzyl)amino]methylene] bisphosphonic acid hydrochloride | — | 9 | 85 | 12 |
| Ex. 41 | CB2 | P,P'-[[(4-Hydrazinobenzyl)amino]methylene] bisphosphonic acid hydrochloride | — | 9 | 25 | 12 |
| Ex. 42 | CB3 | P,P'-[[(4-Hydrazinobenzyl)amino]methylene] bisphosphonic acid hydrochloride | — | 9 | 25 | 12 |
| Comp. Ex. 1 | CB1 | p-Aminobenzoic acid | — | 9 | 25 | 12 |
| Comp. Ex. 2 | CB1 | 4-Hydrazinobenzoic acid | — | 9 | 120 | 24 |
| Comp. Ex. 3 | CB1 | p-Aminobenzoic acid | — | 9 | 80 | 12 |

Evaluation:

The respective production processes of Examples and Comparative Examples were evaluated as follows. Evaluation results are shown in Table 2. The structures of the respective functional groups bonded to the particle surfaces of the self-dispersible pigments are also shown in Table 2. In Table 2, "Ph" means a phenylene group.

Evaluation of Reaction Efficiency:

After 80.0 g of 0.1 mol/l hydrochloric acid was added into 20.0 g of an aqueous dispersion liquid of each self-dispersible pigment to precipitate the self-dispersible pigment, a process of removing a supernatant liquid by centrifugation for 30 minutes at a number of revolutions of 5,000 rpm was repeated twice to obtain a sample. The resultant sample was placed in an oven controlled to a temperature of 60° C. and dried for 18 hours to obtain a dried solid product. The resultant dried solid product was mashed in an agate mortar to weigh out 0.5 g of solids. After 30.0 g of a 0.1 mol/l aqueous solution of sodium hydroxide was added to the solids, and the resultant mixture was agitated for one day, centrifugation was conducted for 60 minutes at a number of revolutions of 80,000 rpm by means of a centrifugal separator (manufactured by BECKMAN COULTER) to collect a supernatant liquid. The resultant liquid was subjected to back titration to determine the amount of the hydrophilic group contained in the functional group bonded to the particle surface of the pigment ("molar number of hydrophilic group in pigment", determined as a value per 1.0 g of the pigment). A potentiometric titration device (trade name "AT-510", manufactured by KYOTO ELECTRONICS MANUFACTURING CO., LTD.) was used in the back titration, in which the dropping amount and time were automatically controlled. In addition, 0.1 mol/l hydrochloric acid (product of Wako Pure Chemical Industries, Ltd.) was used as the titrant.

Upon the production of the self-dispersible pigment, "molar number of hydrophilic group in treatment agent" was calculated from the molar number of the treatment agent used per 1 g of the pigment. This "molar number of hydrophilic group in treatment agent" is the molar number of the hydrophilic group in the treatment agent used per 1 g of the pigment. For example, when a compound having two carboxylic acid groups is used as the treatment agent, the calculation is made with the molar number regarded as being twice of the molar number determined by utilizing the molecular weight of the treatment agent.

Reaction efficiency (%) was calculated on the basis of the following expression (A) from the above-obtained "molar number of hydrophilic group in pigment" and "molar number of hydrophilic group in treatment agent". The value of the reaction efficiency was shown as an integer value by rounding off the value to one's place for convenience's sake.

Reaction efficiency (%)=("Molar number of hydrophilic group in pigment"/"Molar number of hydrophilic group in treatment agent")×100     (A)

The reaction efficiency was evaluated from the calculated reaction efficiency value according to the following evaluation criteria. In the present invention, in the following evaluation criteria, "C" was regarded as an unacceptable level, and "AA", "A" and "B" were regarded as acceptable levels.
AA: The reaction efficiency was 30% or more;
A: The reaction efficiency was 20% or more and less than 30%;
B: The reaction efficiency was 10% or more and less than 20%; and
C: The reaction efficiency was less than 10%.

Evaluation of Image:

After an aqueous dispersion liquid of each self-dispersible pigment and the following respective components (unit: %) were mixed and sufficiently agitated, the resultant mixture was filtered under pressure through a membrane filter having a pore size of 1.2 μm (trade name "HDCII FILTER", product of Pall Corporation) to prepare each ink. "ACETYLENOL E100" is a trade name of a nonionic surfactant (product of Kawaken Fine Chemicals Co., Ltd.).
Aqueous dispersion liquid: 30.0%
Glycerol: 15.0%
Triethylene glycol: 5.0%
ACETYLENOL E100: 0.2%
Ion-exchanged water: 49.8%.

The ink prepared was filled into an ink cartridge, and the ink cartridge was installed in an ink jet recording apparatus (trade name "PIXUS MP480", manufactured by Canon Inc.) in which the ink is ejected from a recording head by the action of thermal energy. In this ink jet recording apparatus, the condition in which the resolution is 600 dpi×600 dpi, and one ink droplet whose mass is 25 ng±10% is applied to a unit region of 1/600 inch×1/600 inch is defined as "the recording duty being 100%". This ink jet recording apparatus was used to record a solid image whose recording duty is 100% on a recording medium (plain paper, trade name "PB PAPER GF-500", product of Canon Inc.). A spectrophotometer (trade name "Spectrolino", manufactured by Gretag Macbeth) was used to measure the optical density of the solid image in the resultant recorded article under the following conditions: light source: D50 and visual field: 2°, and the solid image was visually observed to evaluate the reaction efficiency according to the following evaluation criteria. When the pigment species is an organic pigment, evaluation was made with a numerical value of the optical density shown in the parentheses. In the present invention, in the following evaluation criteria, "C" was regarded as an unacceptable level, and "A" and "B" were regarded as acceptable levels.
A: The optical density was 1.40 (1.10) or more, and the solid image is uniform and steady;
B: The optical density was 1.40 (1.10) or more, but the solid image was somewhat ununiform; and
C: The optical density was less than 1.40 (1.10).

TABLE 2

Evaluation of production process and properties of self-dispersible pigment

| | Reaction efficiency (%) | Evaluation of reaction efficiency | —$R_1$ | Evaluation of image |
|---|---|---|---|---|
| Ex. 1 | 28 | A | —Ph—COONa | B |
| Ex. 2 | 33 | AA | —Ph—(COONa)$_2$ | A |
| Ex. 3 | 25 | A | —Pn(—OH)—COONa | A |
| Ex. 4 | 28 | A | —Ph—SO$_3$Na | B |
| Ex. 5 | 34 | AA | —Ph—PO$_3$Na$_2$ | A |
| Ex. 6 | 27 | A | —Ph—COONa<br>—Ph—SO$_3$Na | A |
| Ex. 7 | 32 | AA | —Ph—COONa<br>—Ph—PO$_3$Na$_2$ | A |
| Ex. 8 | 35 | AA | —Ph—CONH—CH—(PO$_3$Na$_2$)$_2$ | A |
| Ex. 9 | 27 | A | —Ph—CH$_2$—COONa | A |
| Ex. 10 | 26 | A | —Ph—O—CH$_2$—COONa | A |
| Ex. 11 | 17 | B | —Ph—CH(COONa)$_2$ | A |
| Ex. 12 | 28 | A | —Ph—COONa | A |
| Ex. 13 | 27 | A | —Ph—COONa | A |
| Ex. 14 | 23 | A | —Ph—COONH$_4$ | A |
| Ex. 15 | 22 | A | —Ph—COONa | B |
| Ex. 16 | 19 | B | —Ph—COONa | B |
| Ex. 17 | 24 | A | —Ph—COONa | A |
| Ex. 18 | 29 | A | —Ph—COONa | A |

TABLE 2-continued

Evaluation of production process and properties of self-dispersible pigment

|  | Reaction efficiency (%) | Evaluation of reaction efficiency | —$R_1$ | Evaluation of image |
|---|---|---|---|---|
| Ex. 19 | 24 | A | —Ph—(COONa)$_2$ | B |
| Ex. 20 | 26 | A | —Ph—(COONa)$_2$ | A |
| Ex. 21 | 35 | AA | —Ph—(COONa)$_2$ | A |
| Ex. 22 | 37 | AA | —Ph—(COONa)$_2$ | A |
| Ex. 23 | 33 | AA | —Ph—(COONa)$_2$ | A |
| Ex. 24 | 26 | A | —Ph—(COONa)$_2$ | B |
| Ex. 25 | 35 | AA | —Ph—(COONa)$_2$ | A |
| Ex. 26 | 23 | A | —Ph—(COONH4)$_2$ | A |
| Ex. 27 | 38 | AA | —Ph—(COONa)$_2$ | A |
| Ex. 28 | 22 | A | —Ph—(COONa)$_2$ | B |
| Ex. 29 | 24 | A | —Ph—(COONa)$_2$ | A |
| Ex. 30 | 29 | A | —Ph—(COONa)$_2$ | A |
| Ex. 31 | 31 | AA | —Ph—(COONa)$_2$ | A |
| Ex. 32 | 38 | AA | —Ph—(COONa)$_2$ | B |
| Ex. 33 | 16 | B | —Ph—(COONa)$_2$ | A |
| Ex. 34 | 18 | B | —Ph—(COONa)$_2$ | A |
| Ex. 35 | 17 | B | —Ph—(COONa)$_2$ | A |
| Ex. 36 | 38 | AA | —Ph—CONH—CH—(PO$_3$Na$_2$)$_2$ | A |
| Ex. 37 | 33 | AA | —Ph—CONH—CH—(PO$_3$Na$_2$)$_2$ | A |
| Ex. 38 | 32 | AA | —Ph—CONH—CH—(PO$_3$NH4$_2$)$_2$ | A |
| Ex. 39 | 33 | AA | —Ph—CONH—CH—(PO$_3$Na$_2$)$_2$ | A |
| Ex. 40 | 28 | A | —Ph—CONH—CH—(PO$_3$Na$_2$)$_2$ | A |
| Ex. 41 | 32 | AA | —Ph—CONH—CH—(PO$_3$Na$_2$)$_2$ | A |
| Ex. 42 | 31 | AA | —Ph—CONH—CH—(PO$_3$Na$_2$)$_2$ | A |
| Comp. Ex. 1 | 9 | C | —Ph—COONa | C |
| Comp. Ex. 2 | 8 | C | —Ph—COONH$_4$ | C |
| Comp. Ex. 3 | 5 | C | —Ph—COONa | C |

The production process according to the present invention is considered by comparing Example 1 with Comparative Examples 1 and 2. The reaction efficiency of Example 1 is higher than that of Comparative Examples 1 and 2. That is, the production process according to the present invention can modify a pigment into a self-dispersible pigment with a less use amount of the treatment agent and can be said to be an efficient process. In Comparative Example 1, it is considered that decomposition of the treatment agent and coupling reaction between radical species other than the modification of the pigment into the self-dispersible pigment were caused, and moreover the reaction efficiency became low because lots of nitrogen gas bubbles were generated.

Comparison of FIG. 1 with FIG. 2 suggests that the amount of byproducts formed in the process of the production of Self-Dispersible Pigment 1 is small, and the reaction ideally progresses, while the amount of byproducts formed in the process of the production of Comparative Self-Dispersible Pigment 1 is large, and the intermediates formed upon the reaction complicatedly react with each other. Characteristic peaks in the reaction of Self-Dispersible Pigment 1 are the peak at a retention time (RT) of 13.8 minutes (MS=168, positive) and the two peaks at retention times (RT) around 20 minutes (MS=270, negative). It was suggested that these peaks correspond to the compounds having the respective structures illustrated in FIG. 1. The compound of the retention time of 13.8 minutes is a nitrogen-radical-species-derived compound formed by removing a hydrogen atom from 4-hydrazinobenzoic acid which is the treatment agent. In addition, the compound of the retention time around 20 minutes is a diazene-radical-species-derived compound formed by removing three hydrogen atoms from 4-hydrazinobenzoic acid which is the treatment agent. As apparent from the comparison of FIG. 1 with FIGS. 2 and 3, the respective compounds contained in the separate liquid obtained in the process of the production of Self-Dispersible Pigment 1 are not present in the separate liquids obtained in the process of the production of Comparative Self-Dispersible Pigments 1 and 2. This fact suggests that the reaction utilized in the production process according to the present invention is caused to progress by the removal of the hydrogen atom from the treatment agent, the formation of the radical species in association therewith and the addition of this radical species to the particle surface of the pigment. That is, it is suggested that the reaction utilized in the production process according to the present invention is a reaction caused to progress by a mechanism different from that of the conventional production processes for the self-dispersible pigment.

When the self-dispersible pigments produced in Examples were used, all the solid images were high in optical density compared with the cases where comparative self-dispersible pigments produced by using the same pigment species and structures of functional groups in Comparative Examples 1 to 3 as those of the respective corresponding Examples to be compared were used, so that high-quality images could be recorded.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-133777, filed Jun. 30, 2014, which is hereby incorporated by reference herein in its entirety.

What is claimed is:

1. A production process for a self-dispersible pigment, the process comprising a step of bonding a group $R_1$ in the following general formula (1) to a particle surface of a pigment by a radical addition reaction induced by removal of a hydrogen atom from a compound represented by the general formula (1), $$HN=N-R_1 \quad (1)$$

wherein $R_1$ is a group (a) having at least one of an aliphatic group and an aromatic group, and (b) being substituted with at least one hydrophilic group selected from the group consisting of a carboxylic acid group, a sulfonic acid group, a phosphoric acid group, and a phosphonic acid group.

2. The production process according to claim 1, wherein the compound represented by the general formula (1) is formed by removal of a hydrogen atom from a compound represented by the following general formula (2), $$H_2N\text{---}NH\text{---}R_1 \qquad (2)$$

wherein $R_1$ is a group (a) having at least one of an aliphatic group and an aromatic group, and (b) being substituted with at least one hydrophilic group selected from the group consisting of a carboxylic acid group, a sulfonic acid group, a phosphoric acid group, and a phosphonic acid group.

3. The production process according to claim 1, wherein $R_1$ has at least one of (a) a structure containing an arylene group and plural carboxylic acid groups and (b) a structure containing an amide bond and a phosphonic acid group.

4. The production process according to claim 1, wherein the step is conducted in an aqueous system.

5. The production process according to claim 1, wherein the process is conducted at a temperature of 80° C. or less.

6. The production process according to claim 1, wherein the step is conducted in a liquid medium.

7. The production process according to claim 1, wherein the process is conducted in the presence of an oxidizing agent.

8. The production process according to claim 1, wherein the process is conducted at a pH of 1 or more to 13 or less.

9. The production process according to claim 1, wherein the pigment constituting the self-dispersible pigment is at least one of an inorganic pigment and an organic pigment.

10. The production process according to claim 1, wherein the pigment constituting the self-dispersible pigment is a carbon black.

11. A self-dispersible pigment produced by the production process according to claim 1.

12. An ink comprising a self-dispersible pigment, wherein the self-dispersible pigment is the self-dispersible pigment according to claim 11.

13. An ink cartridge comprising an ink and an ink storage portion storing the ink, wherein the ink comprises the ink according to claim 12.

14. An ink jet recording method comprising ejecting an ink from a recording head of an ink jet system to record an image on a recording medium, wherein the ink comprises the ink according to claim 12.

15. A preparation process for an ink, comprising a step of producing a self-dispersible pigment and a step of preparing an ink by mixing components including the self-dispersible pigment, wherein the step of producing the self-dispersible pigment is the production process according to claim 1.

* * * * *